United States Patent
Mueller et al.

(10) Patent No.: US 7,905,871 B2
(45) Date of Patent: Mar. 15, 2011

(54) ELASTICATED MATERIALS HAVING BONDING PATTERNS USED WITH LOW LOAD FORCE ELASTICS AND STIFF CARRIER MATERIALS

(75) Inventors: Joerg Mueller, Karben (DE); Matthias Konrad Hippe, Sulzbach/TS (DE); Cornelia Beate Martynus, Nidderau-Ostheim (DE); Mattias Schmidt, Idstein (DE); Simone Birkmann, Schwalbach (DE); Ralf Geilich, Eppstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 178 days.

(21) Appl. No.: 10/959,747

(22) Filed: Oct. 6, 2004

(65) Prior Publication Data
US 2005/0095942 A1 May 5, 2005

(51) Int. Cl.
*A61F 13/15* (2006.01)
*A61F 13/20* (2006.01)
(52) U.S. Cl. .............................. 604/385.201
(58) Field of Classification Search ............ 428/181, 428/194, 195.01; 604/385.12, 385.09, 385.19, 604/385.24–385.27, 385.201; 442/149
See application file for complete search history.

(56) References Cited

U.S. PATENT DOCUMENTS

| | | |
|---|---|---|
| 2,043,325 A | 6/1936 | Jackson |
| 2,277,043 A | 3/1942 | Cohn |
| 2,532,029 A | 11/1950 | Medoff |
| 2,690,749 A | 10/1954 | Nelson |
| 2,837,095 A | 6/1958 | Stevenson |
| 3,214,323 A | 10/1965 | Russell et al. |
| 3,367,333 A | 2/1968 | Scheier |
| 3,447,536 A | 6/1969 | Snyder |
| 3,468,748 A * | 9/1969 | Bassett ................. 428/198 |
| 3,626,943 A | 12/1971 | Worcester |
| 3,848,594 A | 11/1974 | Buell |
| 3,855,046 A | 12/1974 | Hansen et al. |
| 3,860,003 A | 1/1975 | Buell |
| 3,890,973 A | 6/1975 | Davis et al. |
| RE28,483 E | 7/1975 | Ralph |
| 3,918,433 A | 11/1975 | Fuisz |
| 3,929,135 A | 12/1975 | Thompson |
| 4,324,246 A * | 4/1982 | Mullane et al. ......... 604/366 |

(Continued)

FOREIGN PATENT DOCUMENTS

EP 0 286 543 A2 10/1988

(Continued)

OTHER PUBLICATIONS

Stiffness, Wikipedia Encyclopedia, 2006 online version.*

(Continued)

*Primary Examiner* — Melanie J Hand
(74) *Attorney, Agent, or Firm* — Jay J. Krebs; George H. Leal; Charles R. Matson (57) ABSTRACT

This invention relates to an elasticated materials comprising a stiff carrier material that is satisfactorily elasticated with one or more elastic strands with a low load force, due to the use of a specific bonding pattern, with specific bonding areas. The bonding areas are typically separate bonding areas positioned on separate intervals along the length direction of the carrier material, whereby each bonding area comprises one or more separate bonding zones, extending in the width (X) direction. The invention also relates to absorbent articles comprising this elasticated material and processes for making the elasticated material.

16 Claims, 5 Drawing Sheets

U.S. PATENT DOCUMENTS

| | | | |
|---|---|---|---|
| 4,333,979 A | 6/1982 | Sciaraffa et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,559,051 A | 12/1985 | Hanson | |
| 4,573,986 A * | 3/1986 | Minetola et al. | 604/366 |
| 4,609,518 A | 9/1986 | Curro et al. | |
| 4,610,678 A | 9/1986 | Weisman et al. | |
| 4,610,685 A | 9/1986 | Raley | |
| 4,629,643 A | 12/1986 | Curro et al. | |
| 4,662,875 A | 5/1987 | Hirotsu et al. | |
| 4,662,877 A | 5/1987 | Williams | |
| 4,673,402 A | 6/1987 | Weisman et al. | |
| 4,678,464 A | 7/1987 | Holtman | |
| 4,681,577 A | 7/1987 | Stern et al. | |
| 4,695,278 A | 9/1987 | Lawson | |
| 4,704,116 A | 11/1987 | Enloe | |
| RE32,649 E | 4/1988 | Brandt et al. | |
| 4,778,459 A | 10/1988 | Fuisz | |
| 4,795,454 A | 1/1989 | Dragoo | |
| 4,808,178 A | 2/1989 | Aziz et al. | |
| 4,834,735 A | 5/1989 | Alemany et al. | |
| 4,834,737 A | 5/1989 | Khan | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 4,988,344 A | 1/1991 | Reising | |
| 4,988,345 A | 1/1991 | Reising | |
| 4,990,147 A | 2/1991 | Freeland | |
| 5,062,840 A | 11/1991 | Holt et al. | |
| 5,069,677 A | 12/1991 | Sakurai et al. | |
| 5,137,537 A | 8/1992 | Herron et al. | |
| 5,147,345 A | 9/1992 | Young et al. | |
| 5,151,092 A | 9/1992 | Buell et al. | |
| 5,156,911 A | 10/1992 | Stewart | |
| 5,176,672 A | 1/1993 | Bruemmer et al. | |
| 5,192,606 A | 3/1993 | Proxmire et al. | |
| 5,209,801 A * | 5/1993 | Smith | 156/161 |
| 5,221,274 A | 6/1993 | Buell et al. | |
| 5,260,345 A | 11/1993 | DesMarais et al. | |
| 5,306,266 A | 4/1994 | Freeland | |
| 5,316,836 A * | 5/1994 | Heindel et al. | 428/193 |
| 5,322,729 A | 6/1994 | Heeter et al. | |
| 5,330,459 A | 7/1994 | Lavon et al. | |
| 5,332,897 A | 7/1994 | Stobbe et al. | |
| 5,336,545 A * | 8/1994 | Morman | 428/152 |
| 5,342,338 A | 8/1994 | Roe | |
| 5,344,516 A | 9/1994 | Tanji et al. | |
| 5,382,400 A | 1/1995 | Pike et al. | |
| 5,382,703 A | 1/1995 | Nohr et al. | |
| 5,387,207 A | 2/1995 | Dyer et al. | |
| 5,387,450 A | 2/1995 | Stewart | |
| 5,397,316 A | 3/1995 | Lavon et al. | |
| 5,429,632 A | 7/1995 | Tanji et al. | |
| 5,439,459 A | 8/1995 | Tanji et al. | |
| 5,439,734 A | 8/1995 | Everhart et al. | |
| 5,462,541 A | 10/1995 | Bruemmer et al. | |
| 5,494,736 A | 2/1996 | Willey et al. | |
| 5,514,121 A | 5/1996 | Roe et al. | |
| 5,518,801 A | 5/1996 | Chappell et al. | |
| 5,520,673 A | 5/1996 | Yarbrough et al. | |
| 5,520,674 A | 5/1996 | Lavon et al. | |
| 5,536,555 A | 7/1996 | Zelazoski et al. | |
| 5,567,478 A | 10/1996 | Houben et al. | |
| 5,576,091 A | 11/1996 | Zajaczkowski et al. | |
| 5,576,282 A | 11/1996 | Miracle et al. | |
| 5,607,760 A | 3/1997 | Roe | |
| 5,609,587 A | 3/1997 | Roe | |
| 5,611,791 A | 3/1997 | Gorman et al. | |
| 5,623,888 A * | 4/1997 | Zafiroglu | 112/414 |
| 5,625,222 A | 4/1997 | Yoneda et al. | |
| 5,628,097 A | 5/1997 | Benson et al. | |
| 5,635,191 A | 6/1997 | Roe et al. | |
| H1670 H | 7/1997 | Aziz | |
| 5,643,588 A | 7/1997 | Roe et al. | |
| 5,648,167 A | 7/1997 | Peck | |
| 5,658,639 A | 8/1997 | Curro et al. | |
| 5,667,619 A | 9/1997 | Alikhan | |
| 5,707,950 A | 1/1998 | Kasturi et al. | |
| 5,728,081 A | 3/1998 | Baer et al. | |
| 5,830,203 A | 11/1998 | Suzuki et al. | |
| 5,830,604 A | 11/1998 | Singleton et al. | |
| 5,853,403 A | 12/1998 | Tanzer et al. | |
| 5,858,515 A | 1/1999 | Stokes et al. | |
| 5,876,753 A | 3/1999 | Timmons et al. | |
| 5,888,591 A | 3/1999 | Gleason et al. | |
| 5,902,297 A | 5/1999 | Sauer | |
| 5,919,177 A | 7/1999 | Georger et al. | |
| 5,922,417 A | 7/1999 | Singleton et al. | |
| 5,941,864 A | 8/1999 | Roe | |
| 5,989,478 A | 11/1999 | Ouellette et al. | |
| 5,990,377 A | 11/1999 | Chen et al. | |
| 6,015,936 A | 1/2000 | Takai et al. | |
| 6,045,877 A | 4/2000 | Gleason et al. | |
| 6,168,583 B1 * | 1/2001 | Tanji et al. | 604/385.14 |
| 6,186,992 B1 | 2/2001 | Roe et al. | |
| 6,261,679 B1 | 7/2001 | Chen et al. | |
| 6,353,149 B1 | 3/2002 | Stone | |
| 6,380,456 B1 | 4/2002 | Goldman | |
| 6,395,957 B1 | 5/2002 | Chen et al. | |
| 6,417,425 B1 | 7/2002 | Whitmore et al. | |
| 6,461,430 B1 | 10/2002 | Kwok | |
| 6,465,073 B1 * | 10/2002 | Morman et al. | 428/198 |
| 6,482,191 B1 | 11/2002 | Roe et al. | |
| 6,537,695 B2 | 3/2003 | McLoughlin et al. | |
| 6,569,275 B1 | 5/2003 | Popp et al. | |
| 6,863,959 B2 * | 3/2005 | Welch et al. | 428/198 |
| 7,144,957 B2 | 12/2006 | Funk et al. | |
| 7,223,261 B2 | 5/2007 | Mueller et al. | |
| 2001/0000795 A1 | 5/2001 | Bolian, II et al. | |
| 2002/0029024 A1 | 3/2002 | Furuya et al. | |
| 2002/0049419 A1 | 4/2002 | Mizutani et al. | |
| 2002/0058128 A1 * | 5/2002 | Toyoshima et al. | 428/182 |
| 2002/0087136 A1 | 7/2002 | Widlund | |
| 2002/0119722 A1 | 8/2002 | Welch et al. | |
| 2002/0177632 A1 | 11/2002 | Choi | |
| 2003/0143376 A1 | 7/2003 | Toyoshima et al. | |
| 2003/0171729 A1 | 9/2003 | Kaun et al. | |
| 2004/0092900 A1 | 5/2004 | Hoffman et al. | |
| 2004/0092902 A1 | 5/2004 | Hoffman et al. | |
| 2004/0097895 A1 | 5/2004 | Busam et al. | |
| 2004/0162538 A1 | 8/2004 | Mueller et al. | |
| 2005/0004541 A1* | 1/2005 | Roberts | 604/367 |
| 2005/0095942 A1 | 5/2005 | Mueller et al. | |
| 2005/0177123 A1 | 8/2005 | Catalan | |
| 2005/0215965 A1 | 9/2005 | Schmidt et al. | |
| 2006/0025744 A1 | 2/2006 | Mishima et al. | |
| 2007/0191806 A1 | 8/2007 | Mueller et al. | |
| 2007/0197992 A1 | 8/2007 | Martynus et al. | |

FOREIGN PATENT DOCUMENTS

| | | |
|---|---|---|
| EP | 0 357 298 A2 | 3/1990 |
| EP | 0 433 951 A2 | 6/1991 |
| EP | 312118 B1 | 2/1996 |
| EP | 0 811 479 A2 | 12/1997 |
| EP | 0 934 736 A1 | 8/1999 |
| EP | 0 953 323 A | 11/1999 |
| EP | 0 978 264 A1 | 2/2000 |
| EP | 1 057 464 A2 | 12/2000 |
| EP | 1 106 152 A | 6/2001 |
| EP | 1 184 020 A2 | 3/2002 |
| EP | 1 190 690 A2 | 3/2002 |
| EP | 1201212 A2 | 5/2002 |
| EP | 1 279 388 A1 | 1/2003 |
| EP | 1 403 419 A | 3/2004 |
| EP | 1 520 569 A1 | 4/2005 |
| GB | 2 284 550 A | 6/1995 |
| GB | 2 287 888 A | 10/1995 |
| GB | 2 288 412 A | 10/1995 |
| GB | 2 297 473 A | 8/1996 |
| GB | 2 328 158 A | 2/1999 |
| GB | 2 329 842 A | 4/1999 |
| WO | WO 93/01780 A1 | 2/1993 |

| | | | |
|---|---|---|---|
| WO | WO 93/16669 A1 | 9/1993 |
| WO | WO 9316669 A1 * | 9/1993 |
| WO | WO 95/09261 A1 | 4/1995 |
| WO | WO 95/24173 A2 | 9/1995 |
| WO | WO 96/00549 A1 | 1/1996 |
| WO | WO 96/03501 A1 | 2/1996 |
| WO | WO 9613989 A1 * | 5/1996 |
| WO | WO 98/08476 A1 | 3/1998 |
| WO | WO 98/43587 A1 | 10/1998 |
| WO | WO 98/56326 A1 | 12/1998 |
| WO | WO 99/02393 A1 | 1/1999 |
| WO | WO 99/02395 A1 | 1/1999 |
| WO | WO 99/30661 A1 | 6/1999 |
| WO | WO 99/56680 A1 | 11/1999 |
| WO | WO 99/62446 A1 | 12/1999 |
| WO | WO 00/01334 A1 | 1/2000 |
| WO | WO 0100053 A1 * | 1/2001 |
| WO | WO 01/06974 A1 | 2/2001 |
| WO | WO 02/48440 A2 | 6/2002 |
| WO | WO 03009795 A1 * | 2/2003 |
| WO | WO 2006/031639 A1 | 3/2006 |

OTHER PUBLICATIONS

Amplitude, Wikipedia Encyclopedia, 2006 online version.*
U.S. Appl. No. 11/786,890, filed Apr. 13, 2007, Mueller, et al.
U.S. Appl. No. 11/701,152, filed Feb. 1, 2007, Martynus, et al.

* cited by examiner

ELASTICATED MATERIALS HAVING BONDING PATTERNS USED WITH LOW LOAD FORCE ELASTICS AND STIFF CARRIER MATERIALS

FIELD OF THE INVENTION

This invention relates to an elasticated materials comprising a stiff carrier material that is satisfactorily elasticated with one or more elastic strands with a low load force, due to the use of a specific bonding pattern, with specific bonding areas. The invention also relates to absorbent articles comprising this elasticated material and processes for making the elasticated material.

BACKGROUND OF THE INVENTION

Absorbent articles such as diapers comprise normally one or more components that are elasticated, such as the leg cuffs or waistband. Other absorbent articles, that incorporate an elasticated component, are diapers that have a so-called elasticated anal and/or vaginal cuff. Such cuffs may for example be formed by a topsheet that has one or more large opening(s) to receive fecal material, and guide it to a void space, the topsheet having elastic strands along the opening(s) in the topsheet in order to position the aperture correctly against the wearer's skin such as described in U.S. Pat. No. 6,482,191. Also co-pending application EP-A-1201212 describes a preferred diaper with an elasticated anal and/or vaginal cuff; it is described that it is desirable to have elastics of a specific force profile, to provide the best alignment and fit of the diaper.

Such elastics may be bonded to a for example the topsheet of the absorbent article by use of adhesive or non-adhesive bonding methods, known in the art; for example, well-known methods therefore are described in U.S. Pat. No. 6,461,430 and US2002/0119722.

The inventors have found that it is desirable that the elastics in such anal or vaginal cuff(s) of a diaper have low load force elastics, so that there are no pressure marks on the wearer's skin and the diapers are more comfortable to wear. The inventors also found that the preferred topsheet material is a material that is relatively stiff and/or that the material is for example a nonwoven material with a relatively high content of meltblown fibers. Namely, the preferred anal or vaginal cuff materials generally are air permeable and have high barrier properties. This is in a preferred execution achieved by a nonwoven material that has a low surface energy as well as a small pore size, such as composite nonwoven materials with a high meltblown content (e.g. 5 g/m² or more), and which is by consequence stiff.

However, the inventors have found that the combination of low load force elastics and stiff carrier (topsheet) material is not always possible: the low force elastics are typically not capable to contract the stiff carrier material in the required way.

The present invention is directed to a way of enabling low load force elastics to contract stiff material. Namely, the inventors found that if the elastic strands are applied with a specific bonding pattern to the stiff carrier material, the low load force elastics are nevertheless capable of contracting the stiff material. Unlike the bonding patterns known in the art to bond elastics to other materials, such as the bonding pattern described in U.S. Pat. No. 6,461,430, the specific new bonding pattern is such that there are large open areas between the bonding areas. It is believed that the presence of these large open areas between the bonding areas allows the stiff carrier material to form ridges with a sufficiently large radius of curvature, preferably in more or less the direction of the stretch (e.g. 'more or less' being less than 45° away from the direction of stretch). Thus, the distance between two bonding areas needs to have a certain minimum size, which typically depends on the stiffness of the material, e.g. which becomes larger as the stiffness of the material increases.

Moreover, the specific bonding pattern reduces the random wrinkling of the carrier material, which results in a smoother elasticated material, providing thus more wearer's comfort, e.g. reduced pressure marks on the wearer's skin.

The elasticated carrier material is particularly useful as (part of) an anal or vaginal cuff of a diaper, but it may equally be used in other articles, or as other components of a diaper, such as (part of) the elasticated leg cuffs, elasticated waist band, elasticated fasteners, elasticated backsheet etc.

SUMMARY OF THE INVENTION

The first embodiment of the present invention relates to an elasticated material comprising a carrier material having a longitudinal direction or length $Y_c$, comprising at least one elastic material, typically a strand, that extends over said carrier material substantially parallel to direction $Y_c$ and that is bonded to said carrier material with a bonding pattern of separate bonding areas, whereby:
a) said carrier material has a bending stiffness B (for bending in the direction parallel to $Y_c$) of at least 4 μN*m;
b) said elastic material has an elastic load force of less than 2.0 N at 100% extension; and
whereby the bonding pattern has:
i. a width (X) and a length (Y),
ii. and a multitude of separate bonding areas with a width $X_b$ and positioned on separate intervals along the length (Y) direction;
whereby each bonding area comprises one or more separate bonding zones, extending in the width (X) direction, said zone(s) having a first dimension $X_z$,
said bonding zone optionally being formed from repeating wave-shaped bonding units, having an amplitude A and being connected to one another in the width direction X, each of said units having a first dimension $X_u$;
whereby the smallest distance (D) between two subsequent bonding areas is at least (0.6 mm+60 $N^{-1}$*B), and more preferably at least (0.6 mm+120 $N^{-1}$*B) and most preferably at least (1.2 mm+120 $N^{-1}$*B);
and provided that when repeating wave-shaped units are present, the amplitude A of each unit is less than 0.5×(D).

The specific new bonding pattern is such that there are large open areas between the bonding areas. In a preferred embodiment, the bonding areas are separated, i.e. not connected to one another, typically such that the open areas between the bonding areas are not limited (by bonding) in the direction that is more or less orthogonal to the direction of stretch. This allows the ridges, as mentioned above, to form without being forced into a pillow-like structure, as would take place with the bonding patterns known in the art (such as the known Omega bonding pattern, described in US 2002/0119722).

A second embodiment of the invention relates to an elasticated carrier material as defined above under a) and b) above, but whereby: c) the bonding pattern has (i) a width (X) and a length (Y); and (ii) one or more bonding areas, each area comprising repeating bonding shapes, connected to one another, each shape having a width $X_s$, and a length $Y_s$, whereby the ratio of $Y_s$ to $X_s$ is less than 0.1 and more preferred less than 0.05.

In one embodiment, the pattern may be an Omega pattern, which is however significantly different to the Omega pattern used in the art, since it has a much larger width and a much smaller distance (length) between the repeating bonding shapes (Omega's).

Typically, high basis weight carrier materials have a high bending stiffness. Thus, alternatively, the elasticated materials may be defined as above, with the exception that the carrier material is defined by the meltblown content in the material, namely being basis a meltblown content of at least 5 gram per $m^2$, or even 10 gram per $m^2$ or more, or even 15 grams per $m^2$ or more, and the smallest distance (D; in mm) between two subsequent bonding areas is at least [0.6 mm+M*0.01*(mm*$m^2$/g)+$M^2$*0.005*mm*$(m^2/g)^2$], where M is the meltblown content in $g/m^2$.

If the carrier material is a laminate of layers of materials, whereof more than one layer comprises meltblown fibres, then the meltblown content referred to above is the sum of the meltblown content values of the layers containing meltblown fibres.

The invention also provides absorbent articles, such as diapers and/or training pants, comprising the elasticated material. In a preferred embodiment, the elasticated material is, or forms part of, the anal/vaginal cuff or topsheet, preferably such a cuff or topsheet with one or more large openings to receive fecal matter, as described herein.

DETAILED DESCRIPTION OF THE INVENTION

Bonding Pattern

When used herein, 'substantially parallel' means herein that the specified object or component has at the most an 30° angle with the other specified object or component, said angle preferably being at the most 10° or even at the most 5° or even 0°.

The exact bonding pattern used to bond the elastic material to the carrier material is essential to ensure that the stiff carrier material is still elasticated in the required way by the low load force elastic material.

The bonding pattern has a width direction and dimension, referred to as width (X), and a length direction and dimension, referred to as length (Y), which are perpendicular to one another.

The bonding pattern may be present over the full length of the carrier web, and thus the length of the carrier web $Y_c$ may equal Y (which may be indefinite, as described below); however, typically, the length of the bonding pattern is less than the length of the carrier material.

Also, the bonding pattern may be present over the full width of the carrier material, and thus, $X_c$ may equal the width of the carrier web X; however, typically, the width of the bonding pattern is less than the width of the carrier material.

In a first embodiment of the invention, the bonding pattern comprises a multitude of separate bonding areas, each with a width $X_b$. Each bonding area then extends substantially in the width (X) direction.

Figure 2:
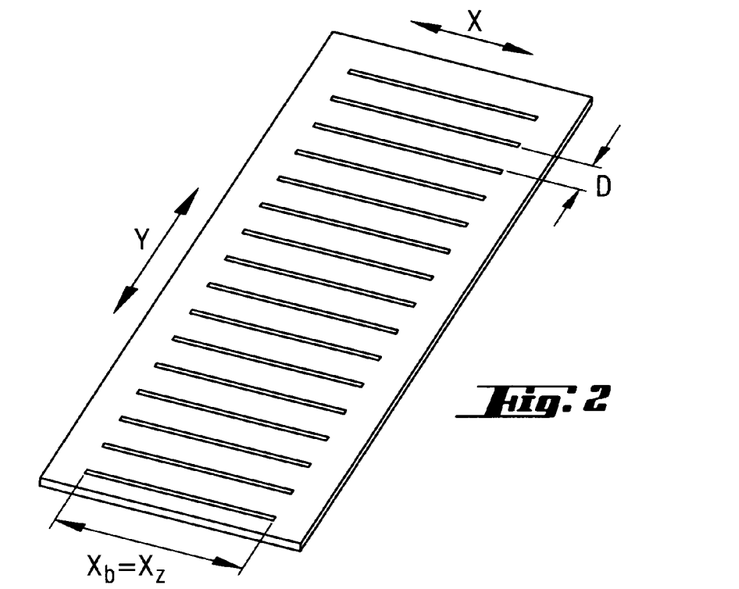
FIG. 2 shows a planar view of a cut-out section (shown as section A in FIG. 1) of an elasticated material (elastic strands not shown), showing a preferred bonding pattern of the material of the invention, comprising a number of separate bonding areas, each consisting of or being equivalent to, one bonding zone.

In this embodiment, the multitude of bonding areas are separated from one another and they are positioned (extend) substantially along the length (direction) of the carrier material, as for example may be seen in FIG. 2.

Each bonding area comprises one or more separate bonding zones, (extending) along substantially the width (X) direction, said zone(s) having a width dimension $X_z$, and a second dimension $Y_z$, preferably substantially parallel to X.

For example, the bonding area may consist of (and thus be equivalent to) one single bonding zone, for example in the form of a single bonding line, typically substantially parallel to X.

Alternatively, the bonding area may also comprise a number of bonding zones, for example a number of bonding dots or lines. In a preferred embodiment, these bonding zones are positioned substantially parallel to X, e.g. having an angle of at the most an 30° angle with X, but the angle being preferably at the most 10° or even 5° or even 0°.

In a first embodiment of the invention, the bonding pattern is such that the smallest distance (D) (in mm) between two subsequent, separated bonding areas is at least (0.6 mm+60 $N^{-1}$*B) and more preferably at least (0.6 mm+120 $N^{-1}$*B) and most preferably at least (1.2 mm+120 $N^{-1}$*B), B being the bending stiffness of the carrier material, as described below.

In a second embodiment of the invention, the smallest distance (D) (in mm) between two subsequent bonding areas is at least 0.6 mm+M*0.01*(mm*$m^2$/g)+$M^2$*0.005*mm* $(m^2/g)^2$, where M is the meltblown content in $g/m^2$. Preferably D is at least 0.9 mm+M*0.01+$M^2$*0.01, or even more preferably D is at least 1.2 mm+M*0.02+$M^2$*0.01.

A bonding zone may optionally be formed from repeating wave-shaped bonding units, each having an amplitude A. Thus, the bonding zone then contains repeating units that are connected to one another in the width direction, each of said repeating units having a width dimension $X_u$.

Then, it is important that the 'open' area between the bonding areas, i.e. the area where there are no bonding areas, is still large, namely such that (when repeating wave-shaped units are present), the amplitude A of each unit is less than 0.5×(D), preferably less than 0.4×(D) or even less than 0.3×(D).

Thus for example, a bonding area may comprise one wavy-line, comprising a number of connected wave-shaped units, provided A is less than 0.5×(D), preferably substantially parallel to X, or oscillating around a line substantially parallel to X.

Figure 6:
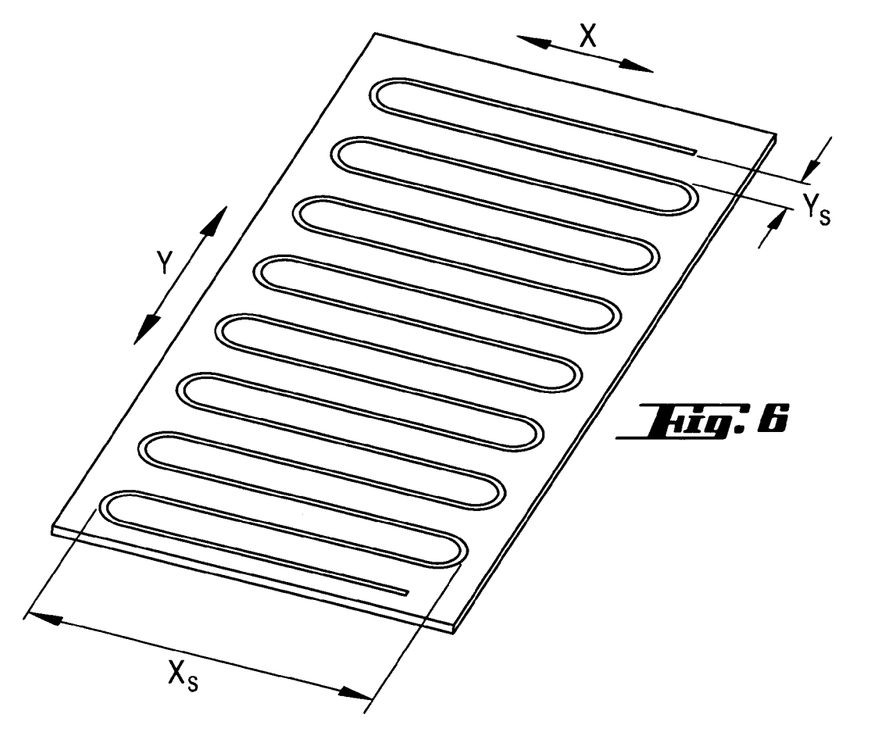
FIG. 6 shows a planar view of a cut-out section of an elasticated material (elastic strands not shown), showing another possible bonding pattern of the material of the invention, comprising a bonding area of repeating wavy shapes that are connected to one another to thus form a very wide (large $X_s$) wavy line.
Figure 7:
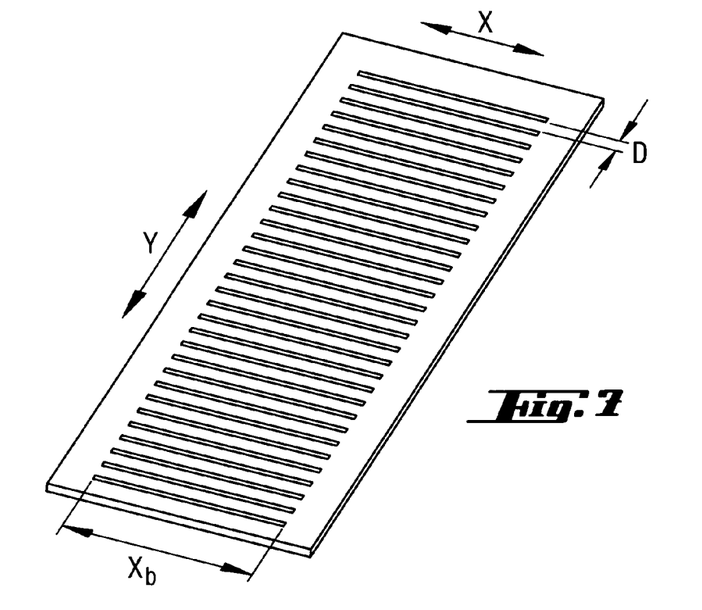
FIGS. 7 and 8 show planar views of exemplary bonding patterns outside the scope of the invention.
Figure 8:
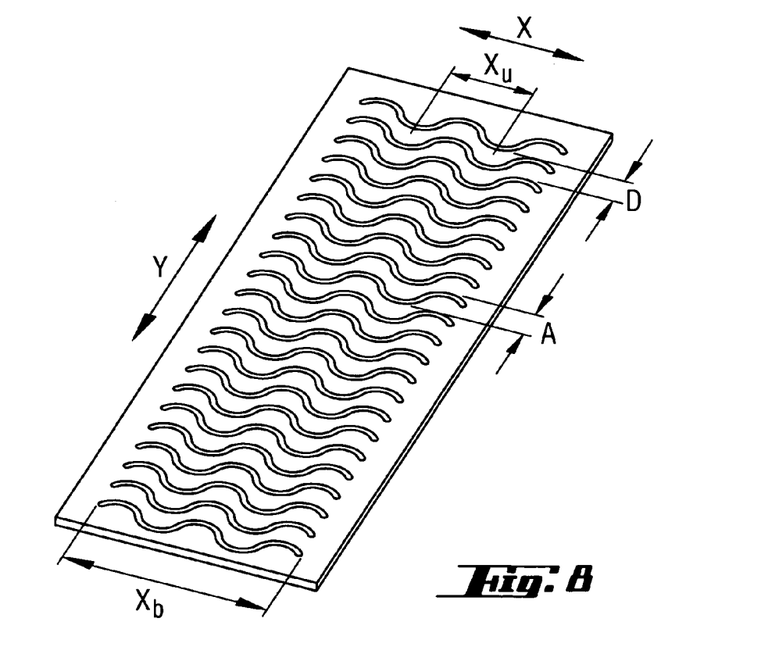

In another embodiment of the invention, the bonding pattern may comprise one or more bonding areas, whereby each bonding area comprises repeating bonding shapes extending both in the X and in the Y direction, such as to form a serpentine line, as may be seen in FIG. 6. Each shape has a width $X_s$, substantially parallel to X, and a length Y, whereby the ratio of $Y_s$ to $X_s$ is less than 0.1, and more preferably less than 0.05.

Thus, unlike the Omega bonding patterns known in the art, the bonding pattern of this embodiment of the invention is very wide, in order to allow the low load force elastics to elasticise the stiff carrier material sufficiently.

Preferred bonding patterns are further exemplified by reference to the figures.

FIG. 2 shows a highly preferred bonding pattern with a multitude of bonding areas, which are completely separate from one another, i.e. not connected. They each have a width $X_b$, which may vary depending on the application of the elasticated material and the width of the elastic material or strands to be applied to, or present on, the bonding pattern. Since each bonding area consist of one bonding zone only, $X_b$ equals Xz. This bonding pattern can be applied by any method described herein, which is suitable to form an intermittent bonding pattern.

The bonding area lines in FIG. 2 may be slightly tilted, e.g. making an angle with the line indicated as X direction. Preferably this angle not more than 30°, preferably no more tan n 20° or even 10°.

As shown in FIG. 2, it is preferred that the 'open area' (i.e. the area between the separate bonding areas, thus not comprising any bonding areas) is not limited in the direction substantially perpendicular to the direction of stretch (which is typically the direction Y).

Figure 3:
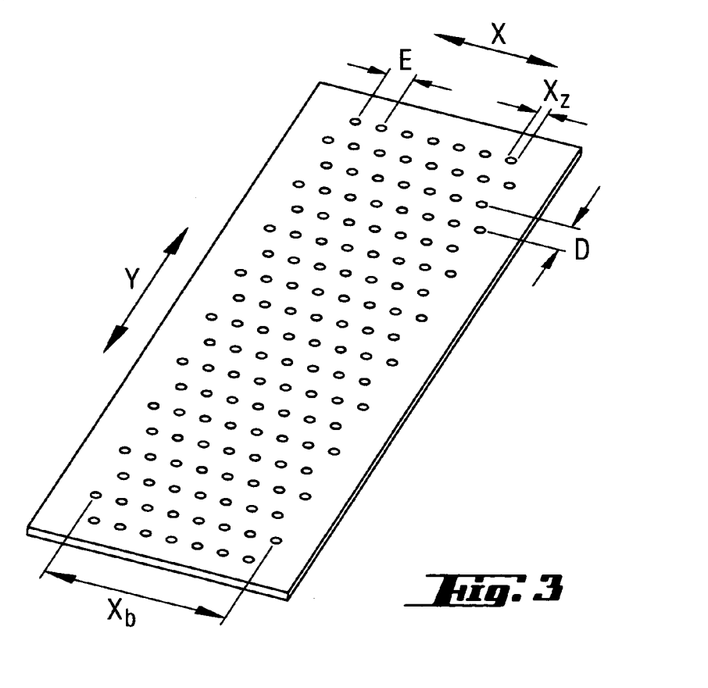
FIGS. 3 and 4 show planar views of a cut-out section of an elasticated material (elastic strands not shown), showing a preferred bonding pattern of the material of the invention, comprising a number of separate bonding areas, each comprising a number of separate binding zones in the shape of dots.
Figure 4:
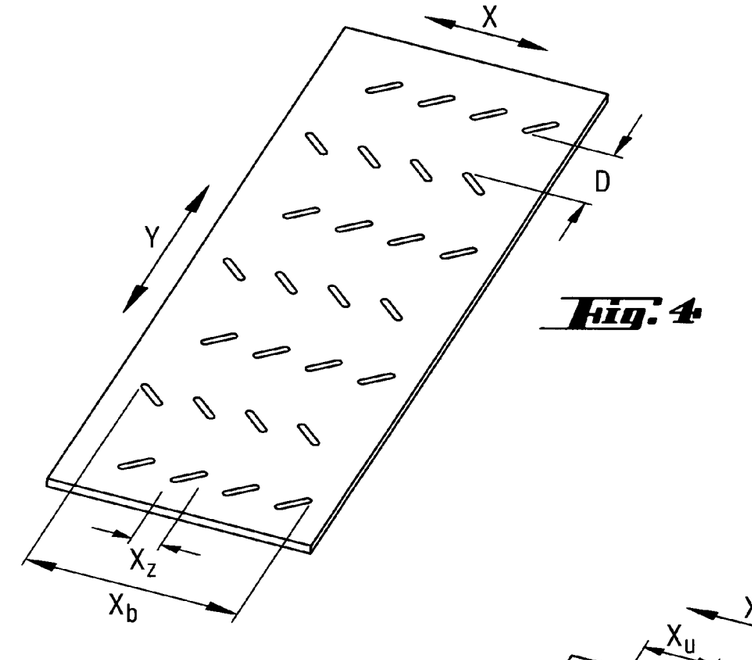

The bonding area lines of FIG. 2 may also be formed from separate bonding zones, such as is shown in FIGS. 3 and 4.

In FIG. 3, it is shown how each bonding area comprises a number of dots, each being a bonding zone, with a width $X_z$. Again, the 'line' formed by a bonding area (line through the bonding zone dots) may be slightly tilted, as described above. The bonding zones in a bonding area may be spaced apart by any distance (E), but preferably the distance (E) is smaller than the distance D, as shown in FIG. 3.

FIG. 4 shows a bonding pattern whereby each bonding area with a width $X_b$ comprises a number of bonding zones, which are tilted lines. Preferably, the angle of such a bonding zone line with the line parallel to $X_b$. is 45° or less, preferably 30° or less. Again, the distance between bonding zones of one bonding area (E; not shown) is preferably less than the distance D between the separate bonding zones.

Figure 5:
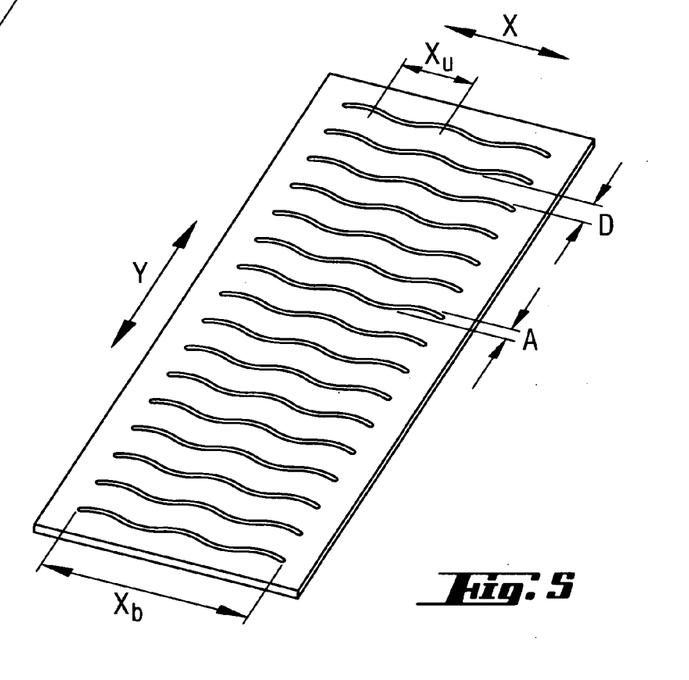
FIG. 5 shows a planar view of a cut-out section of an elasticated material (elastic strands not shown), showing another preferred bonding pattern of the material of the invention, comprising a number of separate bonding areas, each comprising a wave-shaped line with a number (three) of connected bonding units.

FIG. 5 shows another preferred bonding pattern whereby each bonding zone comprises a wave-shaped line of bonding units with a width $X_u$, connected to one another, each repeating unit being a single wave with an amplitude A. In this embodiment, the bonding pattern of the elastic material of the invention is such that A is significantly smaller than D, as described herein above.

Of course, also a mixture of the different bonding areas shown in FIGS. 2 to 5 can be used in a bonding pattern.

FIG. 6 shows another possible bonding pattern of the invention, whereby the bonding area is formed from repeating wavy shapes (about 8 are shown) with a width $X_s$ and a length $Y_s$, whereby $Y_s$ is significantly smaller than $X_s$ as described herein. The thus formed bonding area is in the form of a wavy, serpentine line, or a very wide omega shape, whereby $X_s$ is much greater than $Y_s$, as defined above.

For example, in the embodiment as shown in FIG. 6, the width of the bonding pattern $X_b$ and $X_s$ are preferably at least 3 cm, or even at least 4 cm.

The bonding pattern can be formed by any known bonding method. Preferred are adhesive bonding methods, whereby the adhesive is applied in the bonding pattern on the carrier material or the elastic material (typically on the carrier material), and thereby, the bonding of the carrier material and elastic material is made. Preferred adhesive application methods include adhesive printing, whereby the adhesive is printed in the desired bonding pattern and (intermittent) spraying, e.g. whereby the adhesive is intermittently sprayed in the required pattern, using methods known in the art. The adhesive may also be an activatable adhesive that is, after being applied on the carrier material or the elastic material, only activated in those areas that are to be the bonding areas of the bonding pattern.

The bonding pattern may also be formed by non-adhesive bonding methods, such as ultrasonic bonding, pressure welding or thermal bonding, whereby the ultrasonic radiation, heat and/or pressure is applied such that the desired pattern is formed on the carrier material and/or on the elastic material. Typically the elastic material is hereby applied or positioned in close proximity or contact with the carrier material and the ultrasonic radiation, heat and/or pressure is applied on the combined materials in the desired bonding pattern to form the required bonding areas.

Carrier Material and Elasticated Material

The carrier material herein is a relatively stiff material (e.g. relative to materials commonly used in diapers as for example leg cuffs or topsheets). It may be a material with a relative high basis weight, namely at least of 10 gram per $m^2$ or even at least 15 gram per $m^2$, or even at least 20 gram per $m^2$ or even at least 25 gram per $m^2$.

In one embodiment, it has a bending stiffness of at least 4 μNm, or even at least 8 μNm, or even at least 10 μNm or even at least 12 μNm.

This may be determined by use of a KES-FB2 (pure bending) tester, available from Kato Tech Co Ltd, Japan, following the operating procedures of this equipment.

If the carrier material is not homogeneous, then B is the bending stiffness of the carrier material in the area where it is to carry the elastic material.

If the carrier material is laminate of two or more layers, then B is the sum of the bending stiffness values of all layers. This also applies if the elasticated material is a laminate whereby two carrier materials are connected at least partially via the elastic material bonded to both or all layers of the laminate. Then, the bending stiffness of each layer should be determined and the bending stiffness B as used herein is the sum of the individual bending stiffness values.

The carrier material may be made of any material fulfilling the above criteria. Preferred are woven and non-woven materials of natural fibers (e.g., wood or cotton fibers) and/or synthetic fibers. The carrier material comprises preferably thermoplastic polymer fibers, preferably selected from the group comprising: polyolefins, polyesters, polyurethanes, and polyamides, most preferably the thermoplastic polymer being a polyolefin, most preferably being polypropylene or polyethylene The fibers may be spun bond, carded, wet-laid, melt blown, and/or hydro entangled, and/or otherwise processed as is known in the art. Preferred is that the carrier material comprises a nonwoven material that comprises at least meltblown fibers; preferably the meltblown fibers having a basis weight in said material of at least 5 gram per $m^2$, or even at least 7 gram per $m^2$, or even at least 10 gram per $m^2$ or even 15 grams per m² (the maximum amount being limited by the basis weight of the carrier material as a whole, as defined above).

The carrier material is preferably air permeable. It preferably has high barrier properties. This (together) will enhance the wearer's comfort and at the same time prevent leakage of bodily exudates.

The carrier material preferably has a uniform pore size distribution with small micro-pores, i.e. the carrier material has pores with a maximum pore size (bubble point diameter) of less than 100 µm preferably less than 75 µm more preferable less than 50 µm and most preferably less than 25 µm. The pores are preferably also such that the mean pore size is less than 20 µm, preferred less than 17 µm more preferred less than 13 µm and most preferred less than 10 µm.

It may be preferred that the carrier material is a laminate of two or more sheets or webs. For example, it may comprise at least two layers one of which is a meltblown (M) layer and another is either a spunbond (S) or a carded (C) layer.

Preferred executions are SM SMS, SMMS, SSMS, SSMSS, SSMMS, CM or CMC non-wovens laminates, preferably one web being treated with a surface energy reducing agent described above.

Most preferably, the carded and non-woven webs are formed from polyethylene, polypropylene and/or polybutylene polymer fibers, or (a mixture of) fibers of a copolymers of polyethylene, polypropylene and/or polybutylene; most preferred are polypropylene polymer fibers.

Preferred materials used as carrier material herein are for example a 34 gsm SMS polypropylene non-woven laminates, having a maximum pore size (pore size) of 32 µm, an airpermeability of 34 Darcy/mm, available from Pegas under the name Pegaphob 02 445 032; a 24 gsm SSMMS polypropylene non-woven laminates, having a maximum pore size of 57 µm, for example available from Pegas under the name Pegaphob 02 445 024; a 34 gsm SSMMS polypropylene non-woven laminates, having a maximum pore size of 48 µm, for example available from Pegas under the name Pegaphob 02 445 032; a 20 gsm web available from Sandler under the code VP21/00/75, having a maximum pore size of 22 µm; or a 20 gsm web available from Sandler under the code VP21/00/76, having a maximum pore size of 23 µm. Such materials may for example be treated with Dipolit, to reduce the surface energy of the materials.

The carrier material and/or the elasticated material may be hydrophobic per se or it may be treated to be hydrophobic. This may for example be beneficial when the carrier material is used as (part of) a leg cuff or anal or vaginal cuff, as described hereinafter, in particular in order to isolate the wearer's skin from liquids contained in the remaining part of the absorbent article. Also, any portion of the carrier material and/or the elasticated material may be coated with additional ingredients which help isolate or absorb fecal matter or urine, or with ingredients that are beneficial to the wearer's comfort. For example, the carrier material may comprise a lotion as is known in the art, such as described in U.S. Pat. No. 5,607,760; U.S. Pat. No. 5,609,587; U.S. Pat. No. 5,635,191; U.S. Pat. No. 5,643,588; WO 95/24173.

It may also be preferred that the carrier material and/or the elasticated material comprises ingredients, which reduce friction between the wearer's skin and the carrier material, or in particular between the skin and the elastic strands or elasticated part of the material. Hereto, the carrier or elasticated material may for example comprise on the areas comprising the elastic strands a fine powder, such as talcum powder, or wax.

The material may be treated with an agent to reduce its surface energy. For example useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the material, without reducing the air permeability, can be found in U.S. Pat. No. 5,322,729 and PCT Publication WO 96/03501.

Preferred agents may be selected from the group comprising fluorocarbons, siloxanes, polysiloxanes, preferably including fluorinated monomers and fluorinated polymers, including hexafluoroethylene, hexafluoropropylene and vinyl fluoride and vinylidene fluoride, fluoroacrylate and fluoromethacrylate. Highly preferred is that the topsheet is provided with poly (tetra) fluoroethylene, fluorinated ethylene-propylene copolymers and/or fluorinated ethylene-tetrafluoroethylene copolymers.

The carrier material has a longitudinal dimension $Y_c$, which may equal the length of the carrier material. The carrier material may also be a continuous sheet or web of material (which is subsequently formed in the required shape and size, e.g. by cutting) and then the length may be indefinite.

The width of the carrier material, $X_c$, may be of any size, but it is in practice typically substantially parallel to the cross-machine direction, and width is typically determined by the width of the equipment used to process the carrier material to form the elasticated material.

The elasticated material as used herein is such that it comprises at least one area with the elastic material, as described herein. It may be fully elasticated, such that the surface area of the carrier material corresponds to the surface area of the elastic material. However, preferred is that only part of the carrier material comprises the elastic material and that thus the resulting elasticated material is only partially elasticated.

The bonding pattern on the elasticated material as defined herein is typically such that the elastic material (typically applied in stretched condition to the carrier material) contracts the carrier material such that the resulting elasticated material comprises loops. These loops formed by the elasticated material are preferably relatively large. The average radius of curvature is preferably larger than D/3 or even larger than D/2. The minimum radius of curvature is ideally larger than D/6, or even larger than D/5.

Of course, the radius of the loops may also depend on the stiffness of the carrier material and the elastic load force of the elastic material, and it may also depend on any post processing (e.g. application of pressure during packaging of absorbent articles comprising the elasticated material).

The elastic material or strand(s) may be comprised on the surface of the carrier material or it may be incorporated into the carrier material, for example folded into the carrier material (e.g. the carrier material may be c-folded) or between two layers of the carrier material. In the latter cases, the elastic material may be bonded on both sides to the carrier sheet by the bonding pattern described herein.

The elastic material or strand(s) of the elasticated material may extend over the carrier sheet in a continuous or discontinuous manner. The elasticated material may for example comprise a multitude of elastic strands extending in one line substantially parallel to direction $Y_c$. Alternatively, a single line substantially parallel to $Y_c$ may consist of a single (strand of an) elastic material. Substantially parallel means that the elastic material or strand is positioned substantially parallel to Y, e.g. having an angle of at the most an 30° with Y, but the angle being preferably at the most 20° or even at the most 10° or even 0°.

It may also comprise a multitude of continuous or discontinuous elastic strands substantially parallel to one another, each being substantially parallel to Y. Typically, such strands do then not cross one another.

Per bonding pattern, the elasticated material comprises typically 2 to 20 elastic strands.

The elastic material is typically applied in stretched condition to the carrier sheet.

Generally, the elastic materials are stretched between 100% and 500%, prior to or during application.

In a preferred embodiment the elasticated material is used in or as an anal or vaginal cuff for an absorbent article, as described herein below.

It may be preferred that an anal or vaginal cuff of an absorbent article, including the absorbent articles of the invention, comprises small apertures in at least, or only the front region of the cuff, e.g. the front half or front third of the anal cuff, or most preferably in the front region, from the front end of the opening towards the front waistband.

Therefore, the elasticated material of the invention may also comprise region(s) with small apertures. Typically, such apertures have a surface area of at least 2 mm$^2$, or even at least 3 mm$^2$, but preferably less than 2 cm$^2$ or even less than 1 cm$^2$, or even less than 0.5 cm$^2$.

Elastic Material/strands

The elasticated material herein comprises elastic material. Typically, the elastic material is in the form of one or more strands, that is/are positioned in or on the carrier material.

Typically, the elastic material or strand(s) is positioned substantially parallel to the longitudinal dimension of the bonding pattern Y or the longitudinal dimension $Y_c$ of the carrier material, which is typically the machine direction of the material.

The elastic material has a low elastic load force, namely of less than 2.0 N at 100% extension, preferably less than 1.4 N at 100% extension or even less than 0.8 N at 100% extension, but typically more than 0.3 N at 100% extension.

Preferably, the elastic material has an elastic load force of less than 5.0N at 300% extension, preferably less than 3.0N at 300% extension, but preferably more than 0.5 N or even more than 0.8 N at 300% extension.

This may be measured as follows.

20 separate samples of an elastic material, each 100 mm long and preferably 40 mm wide, are obtained (e.g. by cutting).

Each sample is individually submitted to a one-cycle hysteresis test. Hereby, one sample (i.e. one at a time) is placed in the clamps of a tensile tester, such as a Z10/LH 1S, available from Zwick (Ulm, Germany). The clamps have at least the same width as the width of the elastic material sample in the clamps, so that the clamps at least cover the total width of the elastic material sample in the clamps. The measurement is done in a controlled environment, whereby the temperature is kept constant on 23° C. (+/−2° C.) and the humidity on 50% (+/−2%). The tester uses a load cell of 50N (or less, but at least 10N) and a gage length of 63.5 mm (2.5 inches). The crosshead speed is 508 mm/min. (20 inches/min) when moving upwards and 508 mm/min. (20 inches/min) when moving down wards. The initial load on the sample in the clamps before the test is started is 0.00N to 0.02N.

The one-cycle hysteresis test is than started, stretching the elastic material sample to 100% extension, while measuring the force applied on the sample at the moment of the sample is stretched to 100% extension. Optionally, the forces during stretching and the stretching percentage may be measured as well.

The same test can be done with stretching the elastic material to 300% extension, and measuring the force at that point.

The force value at 100% extension and at 300% extension as used herein is the average force recorded for 20 samples that are submitted to the test above. Thus, the force at 100% extension as used herein is the average force, averaged over 20 recorded forces (for 20 separate samples) at 100% extension.

Preferably, the elastic material has a flat force profile with a small hysteresis effect. Preferred materials include Styrene-Isoprene-Styrene (SIS) and/or Styrene-Ethylene Buthylene-Styrene (SEBS) containing materials (elastomers).

Preferred elastic materials used hereto include materials having an elastic force at 100% extension like 2L-89 or 2L-90 available from Fulflex; most preferred herein are 2L-89 or 2L-90 itself.

The elastic material preferably has a minimum thickness (e.g. gauge) of at least 20 microns, more preferably at least 40 microns, or even at least 60 microns, typically up to about 300 microns, or even up to 200 microns or even up to 150 microns. Highly preferred materials have a thickness of about 70 to 100 microns.

The elastic material generally has a minimum denier between 5 and 1000.

Absorbent Articles

The elasticated materials of the invention are useful in absorbent articles, such as disposable infant diapers, pull-on or training pants, pant-type diapers, incontinence undergarments, absorbent inserts, diaper holders and liners, however, a preferred embodiment of an absorbent article of the present invention is a pull-on or training pants or a diaper, including a diaper (20) shown in FIG. 1 and described hereinafter. Thus, whilst the invention is described in detail with reference to a (baby, infant, or adult) diaper, this description is equally applicable to other wearable disposable article.

Preferably, the elasticated material forms, or is part of, an elasticated component of the absorbent article, such as the leg cuffs, waist band or fasteners of a diaper or training pants, or most preferably, the elasticated material forms or is part of an so-called anal or vaginal cuff or of a so-called elasticated topsheet with one or more openings, herein all referred to as 'cuff'. Such a cuff is shown in FIG. 1 as cuff (21) with preferably one opening (24), although two or more opening may also be used.

The cuff (21) may consist of the elasticated material of the invention or it may comprise the material as part of the cuff (21), for example only in close proximity to the opening (24), e.g. along one or both of the longitudinal edges of the opening (24); and/or along one or both of the transverse edges of the opening (24); and/or for example extending from the opening (24) towards the front and back waist band (22, 23); and/or completely around the opening (24); and/or extending towards the front and/or back waistband (22, 23).

The opening (24) is typically an elongated split opening, leading to a void space. The dimensions of the opening (24) may vary, depending for example on the size of the cuff (21) and/or the article (20). Preferred may be (in particular for size 4 diapers) that the length of the opening (24), in relaxed state, is preferably from 5 to 30 cm, or even from 10 to 25 cm, or even from 12 to 20 cm. The width of the opening (24) of such articles (21), e.g. in a relaxed state, is preferably from 2 to 10 cm, more preferably 3 to 8 cm.

In the fully stretched state, the length of the opening (24) may preferably be from 20 to 35 cm, and the width may preferably be from 3 to 6 cm.

The cuff (21) preferably has at least the elasticated material herein positioned along the two longitudinal edges of the opening (24) (so that each edge comprises elasticated material), extending from said opening towards the first (front; 22) and second (back; 23) waist region or band, preferably such that the end portions of the elastic material can be attached or joined to the waist region or bands (22; 23).

The cuff (21) may be a laminate of the elastic material herein and another material, whereby the elastic material is only present in the regions in close proximity with the opening (24), as described above. Then, the length of the elastic material will typically depend on the size of the cuff (21) and/or of the article (20). For example, for a size 4 diaper, the length of the elastic material in relaxed position may be 10 to 30 cm, or even 15 to 25, whilst in stretched position preferably from 20 to 60 or even 25 to 45 or even 30 to 40 cm.

Preferred is that the elasticated material is such that the center portion(s) of one or more elastic strands are substantially parallel to the center portion(s) of one or more strands, positioned on the other side of the opening (24) (opposing strand(s)). The end portions of the strand(s) on one side of the opening (24) preferably bend away from the end portions of the opposite strand(s), so that the distance between the end portions of the elastic strands is larger than the distance between the centre portions of the elastic strands.

Then, the end portions of an elasticated strand make typically each an angle ($\alpha$ in the back of the diaper (20) and $\beta$ in the front of the diaper (20)) with a line parallel to line Y of between 20° an 40°, and preferably such that the angle between the end portions is about twice as much, e.g. between 40° and 80°. This is herein referred to as an X-shape.

Preferred is that the angle $\alpha$ with the back waistband (23) is larger than the angle $\beta$ with the front waistband (22).

In general, articles with an anal or vaginal cuff with one or more openings to receive bodily exudates that have elastic (elasticated) material along at least two opposing longitudinal edges of such an opening, have specific Cross (Machine) Direction forces, typically due to the positioning of the elastic (elasticated) material and/or the elastic (elasticated) material selected.

Such articles preferably have a preferably a mid cross direction force of at least 0.4N, more preferably of at least 0.6N, or even at least 0.7N; a front CD force of at least 1.0N, or even at least 1.3N, or preferably at least 1.5N; and a back CD force of at least 1.0N, or even at least 1.5N, or even at least 2.2N.

The CD force can be measured as follows:

An absorbent article is placed between the grips of a piece of equipment that can stretch an elastic material very precisely. This is done by fixing the opposing transverse end portions of the article in two opposing grips, e.g. fixing the transverse (cross machine direction) edges of the front and back waistbands in two opposing grips. Then, the article is stretched by pulling the two transverse edges, fixed in the two opposing grips, away from one another, in longitudinal direction with a force of 25N, until the article cannot be further stretched. The length of the article is then measured, which is the fully stretched article length. Subsequently the pressure is released such that the article relaxes back to 75% of the fully stretched article length.

Then, a tensile tester, such as a Zwick, BX1120.25-013, is prepared to measure the (mid, front and back) CD forces in the article. This tester is modified in that it has two grips which are each in the shape of a rectangle with thereto attached a half sphere with a radius of 60 mm, so that the material to be tested will be placed between the half sphere portions of the two grips.

The grip-to-grip distance of the tensile tester is set to be 6 mm, and the tester is set that the grips move only 1 mm towards one another, i.e. to a grip-to-grip distance of 5 mm.

Then, the middle point of a first elastic (elasticated) material along the first longitudinal edge of the opening of the anal or vaginal cuff of the article and the middle point of a second elastic (elasticated) material along the opposing second longitudinal edge of said opening are placed between the grips. Then, the grips are moved 1 mm towards one another, to start the equipment's force measurement. It will measure the mid CD force of the elastic (elasticated) material along the opening of the cuff of the article 9the force exerted by the elastic/elasticated material onto the grip).

This is repeated with 11 identical articles, to obtain an average mid CD force (averaged over the 12 recorded mid CD force values), and this is the mid CD force value referred to herein.

The test may be repeated to obtain the front CD force and the back CD force (again each being an average over 12 recorded values). For the front CD force measurement, the points on the opposing elastic materials, which are each at 20% of the total length of the material, towards the front of the article, are placed between the tensile tester grips. For the back CD force measurement, the opposing points on the opposing elastic materials, which are each at 80% of the total length of the material, towards the back of the article, are placed between the tensile tester grips.

Highly preferred maybe that the articles herein comprise a sheet with small apertures, typically underneath the anal or vaginal cuff, such that the cuff remains the component of the article that is in contact with the skin of the user. Such apertures typically have a surface area of between 1 mm$^2$ and 8 mm$^2$, preferably between 3 mm$^2$ and 5.5 mm$^2$. Preferred is that he sheet with apertures is such that the surface area of the apertures is from 15% to 50%, more preferably from 25% to 40% of the total surface area of the sheet. Preferred apertures sheets are for example described in U.S. Pat. No. 5,658,639 and U.S. Pat. No. 5,628,097.

Highly preferred is that the article (e.g. diaper or training pants) of the invention that has a cuff, also comprises an additional sheet underneath the cuff (e.g. between cuff and backsheet), which serves to immobilize BM.

The additional sheet is preferably made of at least a fibrous web (sheet) which has regions were the fibers are bonded and regions where the fibers are unbonded, so-called bonded and unbonded regions, respectively. The fibers extend from one bonded region through an unbonded region to another bonded region, typically so that the fibers form loops from one bonded region to the next. The bonded regions are such that they form the support structure for the unbonded regions, so that no backing support layer is necessary. The additional sheet is typically a single or unitary sheet or web.

Preferably, the fibers running from the same bonded region to the next same bonded region are about parallel to another. Preferably, the bonded regions are in one plane, e.g. to form a planar support structure, and the fibers extend upward and-.downward out of the plane formed by the bonded region support structure, preferably in the form of loops.

The bonded regions can be in any form, provided said support structure for the unbonded regions is created. For example, a bonded region can be in the form of a dot, square, rectangle, circle, triangle, or line. A number of bonded regions can also be such that they together form a line of not connected dots, squares, lines or strips etc. In the latter case, the bonded regions should be close enough together to ensure that sufficient bonding is achieved to provide the support structure for the unbonded regions.

The unbonded regions may also for example be circular or round, square, rectangular, triangular, diamond-shaped, or hexagonal and/or oval.

Preferably the (largest convex) surface area within the unbonded region is at least 2 mm$^2$, preferably at least 5 mm$^2$ or even at least 10 mm$^2$, or even at least 20 mm$^2$ or even at least 25 mm$^2$, or even at least 30 mm$^2$, and typically up to 200 mm$^2$, or even up to only 100 mm$^2$.

The bonded regions have a certain width dimension, which is, when used herein, the smallest distance between two opposing sides of a bonded regions, in the plane which the bonded regions support structure forms (i.e. thus not the thickness dimension of the bonded regions. Typically, this width dimension is less than 3 mm, or even less than 2 mm, or even less than 1 mm, or even less than 0.8 mm, or even less than 0.5 mm.

The total surface area relationship between the total surface area of the unbonded regions and of the bonded regions is preferably: 20:1, or even 15:1, or even 10:1; or even 8:1, but preferably more than 2:1, or even more than 3:1.

Preferably, the bonded regions are in the form of lines, whereby preferably each bonded region (line) crosses at least one another bonded region (line). Preferably, the bonded regions are positioned in both longitudinal and transverse direction, preferably parallel to one another in each respective direction, as can be seen in FIG. 4a.

The additional sheet may have any basis weight, but preferably, this is from about 10 to 45 g/m$^2$, or even from 20 to 40 g/m$^2$, or even from 30 to 35 g/m$^2$.

A highly preferred additional sheet comprises or consists of a web with a caliper of about 0.25-0.29, preferably about 0.27 mm, compression resistance of about 40-60%, preferably about 55%, a basis weight of about 28-34 g/m$^2$, preferably about 32 g/m$^2$, with preferably unbonded regions of about 22 mm$^2$ to 30 mm$^2$, preferably about 25 mm$^2$, and bonded regions with a maximum width of 0.7 mm to 1.1 mm, preferably 0.9 mm, in the shape of crossing lines. Highly preferred additional sheets are available from Sandler with the trade name: VP 3001/11-32 gsm.

The disposable, wearable absorbent article, e.g. diaper or training pants, of the invention has typically a backsheet that is liquid impervious and breathable and thereto air permeable or even moisture-vapor permeable. Any material known to be suitable as backsheet can be used herein. The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. SELF webs suitable for the present invention are more completely described in U.S. Pat. No. 5,518,801.

Typically, also an absorbent core is present, which is preferably positioned between at least a portion of the backsheet and cuff, when both present.

The absorbent core may comprise any absorbent material which is generally compressible, conformable, non-irritating to the wearer's skin, and capable of absorbing and retaining liquids such as urine and other body exudates, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; more preferably included (at least) super absorbents (super absorbent polymers); absorbent gelling materials; or any other known absorbent material or combinations of materials. Exemplary absorbent structures for use as the absorbent core are described in U.S. Pat. No. 4,610,678; U.S. Pat. No. 4,673,402; U.S. Pat. No. 4,834,735; U.S. Pat. No. 4,888,231; U.S. Pat. No. 5,137,537; U.S. Pat. No. 5,147; U.S. Pat. No. 5,260,345; U.S. Pat. No. 5,387,207; and U.S. Pat. No. 5,625,222.

The article, e.g. diaper, of the invention may have side panels, one or more leg cuff per leg opening, that provide improved containment of liquids and other body exudates. The leg cuff and/or side panels may be formed or comprise the elasticated material of the invention. Leg cuffs may also be referred to as leg bands, side flaps, barrier cuffs, or elastic cuffs, as described in; U.S. Pat. No. 3,860,003; U.S. Pat. Nos. 4,808,178 and 4,909; U.S. Pat. Nos. 4,695,278 and 4,795,454.

Typically, the waist regions of the diaper have a portion, which is or forms the waistband. In FIG. 1, this is shown as front waistband (22) and back waistband (23), forming together 'the waistband'. The waistband may be formed from or comprise the elasticated material of the invention.

Figure 1:
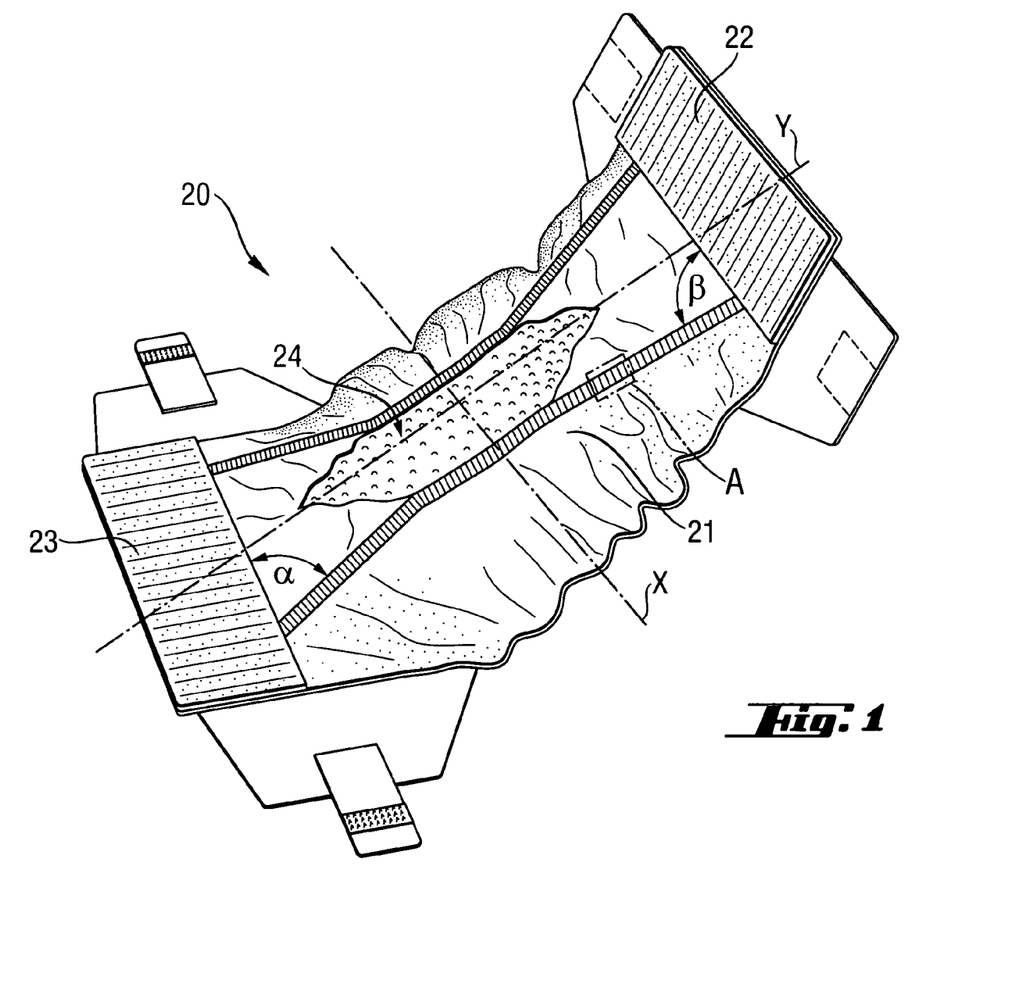
FIG. 1 is a perspective view of a preferred diaper comprising an anal/vaginal cuff comprising the elasticated material of the invention.

In one type of diapers, as shown in FIG. 1, the waistband is open prior to use and needs fastening around the waist of the wearer. Thereto, the diaper preferably has a fastening system, typically joined to the waist region or band. The fastening system may comprise the elasticated material of the invention.

The fastening system preferably maintains the front waistband and the back waistband in a touching or overlapping configuration so as to provide lateral tensions or force line about the circumference of the diaper to hold the diaper on the wearer. The fastening system preferably comprises tape tabs and/or hook and loop fastening tabs, although any other known fastening means are generally acceptable. Some exemplary fastening systems are disclosed in U.S. Pat. No. 3,848,594; U.S. Pat. No. 4,662,875; U.S. Pat. No. 4,846,815; U.S. Pat. No. 4,894,060; U.S. Pat. No. 4,946,527; U.S. Pat. No. 5,151,092; and U.S. Pat. No. 5,221,274; and U.S. Pat. No. 4,963,140.

A preferred additional component of the absorbent articles herein is a transverse barrier (in cross machine direction), placed in the back region of the article, typically close to the back waistband, that stops bodily exudates (e.g. fecal matter) to leak out of the article via the back waistband.

What is claimed is:

1. An absorbent article comprising:
   a backsheet;
   a topsheet connected with the backsheet and having longitudinally opposing first and second waist regions, the topsheet comprising a carrier material having a bending stiffness B of at least 4 μN*m to about 12 μN*m;
   a void space between the topsheet and the backsheet for receiving bodily exudates;
   an opening in the topsheet providing access to the void space, the opening having longitudinally extending first and second side edges;
   first and second laterally opposing elasticated regions disposed adjacent respective first and second side edges of the opening, the first and second laterally opposing elasticated regions extending from the first waist region to the second waist region, wherein the first and second laterally opposing elasticated regions are parallel to each other along the first and second side edges of the opening and laterally diverge from each other in the first and second waist regions; and
   wherein the first and second laterally opposing elasticated regions each comprise an elastic material having a length defined along a direction of stretch, wherein the elastic material is bonded to the carrier material in a plurality of bonding areas spaced apart from each other along the length defined along the direction of stretch of the elastic material, wherein the elastic material has an elastic load force of less than about 2.0 N at 100% extension and wherein a distance D along the length of the elastic material defined along the direction of stretch between adjacent bonding areas is at least (0.6 mm+60 $N^{-1}$*B) to about (1.2 mm+120 $N^{-1}$*B);

2. The absorbent article of claim 1, wherein first end portions of the first and second side edges of the opening converge toward each other to define an end point of the opening in the first waist region.

3. The absorbent article of claim 1, wherein the carrier material comprises a nonwoven web having a basis weight of at least 10 grams per $m^2$.

4. The absorbent article of claim 3, wherein the nonwoven web has a meltblown content of at least 10 grams per $m^2$.

5. The absorbent article of claim 1, wherein the elastic material has an elastic force at 100% extension in the range of about 0.3 N to about 0.8 N.

6. The absorbent article of claim 1, wherein the elastic material is bonded to the carrier material by applying pressure to the elastic material and the carrier material in the bonding areas.

7. The absorbent article of claim 1, wherein the elastic material is bonded to the carrier material by applying adhesive to the elastic material and the carrier material in the bonding areas.

8. The absorbent article of claim 1, wherein each bonding area comprises at least one bonding zone defined by repeating wave-shaped bonding units having an amplitude A that is less than about (0.5 *D).

9. The absorbent article of claim 1, wherein each bonding area comprises a single bonding zone defined by a line extending along a width of the elastic material.

10. The absorbent article of claim 1, wherein each bonding area comprises a plurality of dot-shaped bonding zones.

11. The absorbent article of claim 1, wherein the elastic material comprises at least one elastic strand.

12. An absorbent article comprising:
a backsheet;
a topsheet connected with the backsheet and having longitudinally opposing first and second waist regions, the topsheet comprising a carrier material having a meltblown content M of at least about 5 grams per $m^2$ to about 15 grams per $m^2$;
a void space between the topsheet and the backsheet for receiving bodily exudates;
an opening in the topsheet providing access to the void space, the opening having longitudinally extending first and second side edges;
first and second laterally opposing elasticated regions disposed adjacent respective first and second side edges of the opening, the first and second laterally opposing elasticated regions extending from the first waist region to the second waist region, wherein the first and second laterally opposing elasticated regions are parallel to each other the along the first and second side edges of the opening and laterally diverge from each other in the first and second waist regions; and
wherein the first and second laterally opposing elasticated regions each comprise an elastic material having a length defined along a direction of stretch, wherein the elastic material is bonded to the carrier material in a plurality of bonding areas spaced apart from each other along the length defined along the direction of stretch of the elastic material, wherein the elastic material has an elastic load force of less than about 2.0 N at 100% extension and wherein a distance D along the length of the elastic material defined along the direction of stretch between adjacent bonding areas is at least 0.6 mm+M*0.01*(mm*$m^2$/g)+$M^{2*}$0.005* mm * ($m^2$/g$)^2$) to about (1.2 mm +M*0.02*(m*$m^2$/g)+$M^2$*0.01* ($m^2$/g$)^2$).

13. The absorbent article of claim 12, wherein first end portions of the first and second side edges of the opening converge toward each other to define an end point of the opening in the first waist region.

14. The absorbent article of claim 12, wherein the elastic material has an elastic force at 100% extension in the range of about 0.3 N to about 0.8 N.

15. The absorbent article of claim 12, wherein the elastic material is bonded to the carrier material by applying adhesive to the elastic material and the carrier material in the bonding areas.

16. The absorbent article of claim 12, wherein each bonding area comprises at least one bonding zone defined by repeating wave-shaped bonding units having an amplitude A that is less than about (0.5*D).

* * * * *